United States Patent [19]

Armstrong

[11] 3,962,125

[45] June 8, 1976

[54] MULTI-PURPOSE DILUENT FOR USE IN BLOOD ANALYSIS BY ELECTRONIC INSTRUMENTATION OF THE COULTER TYPE

[75] Inventor: Douglas Armstrong, Coral Springs, Fla.

[73] Assignee: Coulter Diagnostics, Inc., Hialeah, Fla.

[22] Filed: Jan. 13, 1975

[21] Appl. No.: 540,584

[52] U.S. Cl. ............................... 252/408; 23/230 B
[51] Int. Cl.² .......................................... G01N 33/16
[58] Field of Search........... 252/408, 380; 23/230 B; 424/151

[56] References Cited
OTHER PUBLICATIONS

Davidsohn and Henry: "Clinical Diagnosis by Laboratory Methods," W. B. Saunders Co., 1969, p. 141.
Frankel, Reitman, and Sonnerwirth: "Gradwohl's Clinical Laboratory Methods and Diagnosis"; Mosby, (1970), vol. 1 (pp. 26, 455), vol. 2 (p. 1557), The Merck Index, 8th Edition, (1968), p. 813.

Primary Examiner—Benjamin R. Padgett
Assistant Examiner—David Leland
Attorney, Agent, or Firm—Silverman & Cass, Ltd.

[57] ABSTRACT

A multi-purpose blood diluent for use in electronic enumeration of red and white blood cells and the determination of hemoglobin concentration and other classic parameters, mean cell volume and other measurements of blood cells and particles or measurements of blood cells and particles by means of particle analysis instrumentation of the Coulter type. The blood diluent is characterized as azide free, unreactive and osmotically balanced so as to be capable of affording reproducible and accurate hematological test results. The diluent employs an antibacterial agent which prevents adverse bacterial or fungi growths capable of interference with accurate counts and sodium fluoride to achieve stable conditions in red blood cell volume and aid in the complete conversion of hemoglobin in cyanmethemoglobin for hemoglobin determinations.

9 Claims, No Drawings

MULTI-PURPOSE DILUENT FOR USE IN BLOOD ANALYSIS BY ELECTRONIC INSTRUMENTATION OF THE COULTER TYPE

BACKGROUND OF THE INVENTION

The invention concerns a blood diluent for blood cell counting and sizing and more particularly, a multipurpose blood diluent for use in hematological enumeration of blood cells and the determination of hemoglobin concentration and their collective indices by electronic particle analysis using a Coulter scanning device. Accordingly, the diluent comprises a stable water solution of chemical salts providing an electrolytic solution to which a blood sample can be added so as to dilute the larger number of red blood cells, white blood cells and other blood components and enable the desired parameters of these blood components to be measured, counted and estimated.

It is a common medical diagnostic procedure to analyze and test a blood sample of a patient in order to make certain classic determinations with respect to the blood sample. This procedure is an important tool for the physician. Six characteristically important parameters are referred to as red blood cell count (RBC), the hematrocrit (HCT), the hemoglobin (HGB), the mean corpuscular volume (MCV), the mean corpuscular hemoglobin (MCH) and the mean corpuscular hemoglobin concentration (MCHC). A seventh important determination is white blood cell count (WBC). An instrument which will accept a patient's blood sample and process the sample automatically and continuously to provide the parameters or determinations enumerated is described and claimed in U.S. Pat. No. 3,549,994. Said U.S. Pat. No. 3,549,994 provides acceptable definitions of said parameters and illuminates the problems to be solved in the handling of the blood sample as it is drawn through the fluid system of said patented apparatus.

Coulter Electronics, Inc. of Hialeah, Florida also manufacturers and sells other blood cell counting and analyzing instruments which are less sophisticated than the apparatus of said U.S. Pat. No. 3,549,994 but which are operated to determine red blood cell and white blood cell counts, hemoglobin concentration and their collective indices such as HCT, MCV, MCH and MCHC. The multi-purpose blood diluent embodying the invention is suitable for use with such other instrumentation as well, where problems attendant the successful handling of the blood sample are the same. In other words, this blood diluent is compatible with other electronic particle analysis instruments utilizing the Coulter principle. Such instruments may be referred to herein, at times, collectively by the registered trademark "COULTER COUNTER" owned by Coulter Electronics, Inc.

To contribute to a fuller understanding of the invention, it is helpful to appreciate certain characteristics of red blood cells. Red blood cells are biconcave discs generally toroidal in shape, much like a doughnut. The intermembrane is elastic. Hemoglobin and other components are contained in the interior of the cell. The specific parameters of the red blood cell which it is clinically desirable to measure by the electronic instrumentation using the Coulter principle dictate the necessary characteristics of a suitable diluent.

For instance, it is desirable to know the volume within the red blood cell. Once this measurement is ascertained and the red blood cells have been counted, the packed cell volume or Hematocrit (HCT) can be computed. The diluent of the invention therefore must be an electrolyte which enables electronic measurements to be made by the Coulter type instrument. The diluent of the invention also should be capable of equilibrating and stabilizing the volume of red blood cells in the sample so that its cubic volume can be measured, namely, MCV.

As explained in said U.S. Pat. No. 3,549,994, the enumeration of blood cells by the "Coulter Counter" requires accurate and successful dilution of the blood sample drawn into its fluid system. Such analysis predicates certain diluent specifications essential to the successful and proper performance of the apparatus. For instance, the diluent must be capable of maintaining the chemical and physical integrity of blood corpuscles prior to and during the assay procedure. The blood cells are required to retain the same physical character in the diluted solution as exhibited in the undiluted sample. For this purpose, the blood diluent must be isotonic and osmotically balanced relative the solutions in the blood cells. The resistance of the red blood cells to lysing for purposes of hemoglobin determinations must not be altered in any way by the blood diluent. The blood diluent must not interfere in any way with the process of converting the hemoglobin released to a quantitatively determinative hemoglobin compound, such as, cyanmethemoglobin, so that the accuracy of the hemoglobin determination will not be compromised.

A suitable blood diluent must be devoid of foreign particulate matter because the presence of foreign particles will result in the enumeration thereof as a blood cell or constituent. Thus, the blood diluent must be filtered free of particles exceeding 0.2 micron diameter at the time of manufacture. Concomitantly, the diluent must be bacteriostatic in nature so as to prevent the growth of microorganisms after packaging of the diluent. It has been recognized that a proper blood diluent for use with such electronic particle analysis apparatus and hemoglobinometer instruments must be unreactive and osmotically balanced if reproducible, accurate results are to be obtained.

Such electrolyte solutions used in blood cell counting and sizing are required to be of such concentration that the electrolyte ions exert an osmotic pressure equal to that of the intracellular fluid. If the cells are suspended in a solution of reduced osmotic pressure, i.e., hypotonic, the cells will absorb water and expand until burst thereof releases the cell fluids into the solution. This condition is called "hemolysis". Where blood cells are suspended in an electrolyte solution of increased osmotic pressure, cellular fluid will be lost to the solution thereby shrinking the volume of the cell. This condition is called "crenation". Although preservatives for preventing bacterial or fungal growth are desirable, caution must be observed to avoid increasing the cell volume of blood cells in suspension by reason of the preservative used.

THE PRIOR ART

A blood diluent hertofore available from Coulter Electronics, Inc. was sold under the registered trademark "ISOTON" owned by Coulter Diagnostics, Inc. of Hialeah, Florida, a subsidiary company. Although this blood diluent has been used with the Coulter Counters and hemoglobinomenters successfully for many years, it did have certain undesirable features which are eliminated by the herein invention.

One undesirable feature was the use of sodium azide as the effective bacteriostatic agent. Sodium azide, incidentally, was commonly used in isotonic blood diluents. Sodium azide is a relatively high toxic material so that aqueous solutions of the azide and vapors of hydrozoic acid were required to be taken into account as possibly contributing to adverse physiological effects on laboratory workers exposed to same. In the case of plumbing systems using copper and lead pipes and joints through which the azide solutions must be drained, it is necessary to exercise prudent and judicious flushing procedures to prevent excess accumulations of heavy metal azides over extended periods of time. Consequently, it has been known to be desirable to be able to replace sodium azide with an equally effective bacteriostatic material or agent, but this has not been realized until the advent of this invention.

The use of sodium chloride, potassium chloride and sodium hydroxide in such prior blood diluents has been known. Also known was the use of a chelating agent which in cooperating with the phosphate salt employed served as buffering agents to achieve a desired pH range in which the diluent was operative. Such a chelating agent was ethylenediaminetetracetic acid (EDTA).

SUMMARY OF THE INVENTION

The primary object of the invention is to provide a multi-purpose, electrolytic solution for use in hematological enumeration of blood cells and the determination of hemoglobin concentration and other important parameters of a blood sample by means of automated electronic particle analysis apparatus of the type using the Coulter principle, said solution being osmotically balanced for mean cell volume stability, being azide-free and containing sodium flouride for aiding in hemoglobin conversion to cyanmethemoglobin.

Another important object of the invention is to provide a blood diluent of the character described which can be used successfully with existing Coulter particle analysis apparatus and which is compatible with their present calibration for making such hematological analysis.

The blood diluent embodying the invention successfully substitutes a non-toxic and more compatible bacteriostatic agent for sodium azide without diminution in effectiveness. Further, said diluent is osmotically balanced and unreactive so as to eliminate any interference with the required chemical conversion of hemoglobin materials to cyanmethemoglobin for proper hemoglobin concentration determinations contemplated by the apparatus in question. The diluent also successfully uses a buffering agent containing an anticoagulant and bacteriostatic agent. The anticoagulant prevents agglutination of red blood cells where the blood sample contains abnormal plasma proteins or prevents precipitation of heavy metal salts in the diluent which results in inaccurate counts.

DESCRIPTION OF PREFERRED FORMULATION

An example of the multi-purpose blood diluent embodying the invention is as follows:

| | | Approximate amounts |
|---|---|---|
| 1. | Sodium chloride | 7.936 grams/liter |
| 2. | Potassium choride | 0.4 " |
| 3. | Sodium di-hydrogen phosphate | 0.19 " |

-continued

| | | Approximate amounts |
|---|---|---|
| 4. | Di-sodium phosphate | 1.922 " |
| 5. | Sodium ethylenediamine tertracetic acid (EDTA) | 0.3 " |
| 6. | Sodium fluoride | 0.5 " |
| 7. | 2-phenoxyethanol | 3.3 " |
| 8. | Distilled $H_2O$ | quantity to produce one liter |

The diluent specified above is adjusted to a pH of 7.2 – 7.5 by the suitable buffering agent, EDTA and phosphate salt. The osmolality of the blood diluent is maintained at 320 – 340 milliosmoles.

The desirable characteristic of osmotic balance is procured through the judicious use of both sodium and potassium chloride. Buffering with use of sodium hydroxide is eliminated herein.

The bacteriostatic agent which replaces heretofore utilized sodium azide is 2-phenoxyethanol. This agent is substantially less toxic than sodium azide and hence completely eliminates the problem of possible adverse toxic effects applicable to laboratory technicians. Also, 2-phenoxyethanol does not form any known hazardous substances with copper and lead commonly used in water drainage systems.

The diluent still remains totally unreactive and osmotically balanced for mean cell volume and the phosphate salts coordinate with the EDTA for buffering effectiveness. The EDTA also serves as an anti-coagulant. The sodium fluoride services to stabilize red blood cell volume and aid in converting hemoglobin to cyanmethemoglobin for hemoglobin determinations.

There is produced a blood diluent solution which is an electrolyte capable of conducting current, which stabilizes the red blood cells so that their cubic volume can be accurately measured, which has no adverse effect on white blood cells and can function as an electrolyte for counting white blood cells bu electronic methodology, has no effect on blood platelets and does not interfere with the conversion of hemoglobin to the cyanmethemoglobin form in which hemoglobin is measured.

Preparation of the diluent does not require any special procedures or any special order of addition of ingredients to the water. Consequently, the invention does not concern any methodology in formulation of the diluent. The mixture of ingredients is done mechanically by moderate stirring over a one to two hour period. The solution then is filtered through a 0.2 micron filter and storable in plastic containers directly.

Although preferred formulation has been specified above, the range of pH and osmolality may be broadened for useful purposes. Thus, the pH range may be maintained from between pH of 7.0 to 8.0. Likewise, the useful range of osmolality can be between 300 to 380 milliosmoles. This can be accomplished by varying the amount of active ingredients used for the purpose as specified herein.

It will be appreciated by the skilled artisan that the diluent herein is used with a blood sample in the same manner as said prior ISOTON formulation was used in a Coulter type electronic particle analyzer. However, the blood diluent hereof avoids the adverse problems attendant us of such prior diluent.

What it is desired to claim is:

1. A multi-purpose blood diluent, which is both isotonic and osmotically balanced relative to the solutions in blood cells, to be analyzed for a plurality of classic parameters in an electronic particle analysis apparatus of the Coulter type consisting essentially of:
- a. an osmotically balanced solution of sodium chloride, potassium chloride, sodium di-hydrogen phosphate and di-sodium phosphate,
- b. sodium fluoride,
- c. 2-phenoxyethanol,
- d. an ethylenediamine tetracetic acid, said diluent being an aqueous electrolytic solution maintained at a pH of between 7.0 to 8.0 and at an osmolality of between 300 and 380 milliosmoles, and wherein the sodium fluoride services to stabilize red blood cell volume and aid in converting hemoglobin to cyanmethemoglobin for hemoglobin determination.

2. The blood diluent of claim 1 in which one liter of diluent solution contains approximately 7 grams of sodium chloride and approximately 0.4 grams of potassium chloride.

3. The blood diluent of claim 1 in which the pH range maintained is between 7.2 and 7.5.

4. The blood diluent of claim 3 in which the osmolality is maintained between 320 and 340 milliosmoles.

5. The blood diluent of claim 1 which is free of particles exceeding 0.2 micron diameter.

6. The blood diluent of claim 1 in which the ethylenediamine tetracetic acid is in the form of sodium ethylenediamine tetracetic acid.

7. The blood diluent of claim 5 in which the concentration of the sodium ethylenediamine tetracetic acid is approximately 0.3 grams per liter.

8. The blood diluent of claim 1 in which the concentration of the sodium fluoride is approximately 0.5 grams per liter.

9. The blood diluent of claim 1 in which the concentration of 2-ethoxyethanol is approximately 3.3 grams per liter.

\* \* \* \* \*

UNITED STATES PATENT AND TRADEMARK OFFICE
CERTIFICATE OF CORRECTION

PATENT NO. : 3,962,125
DATED : June 8, 1976
INVENTOR(S) : Douglas Armstrong

It is certified that error appears in the above-identified patent and that said Letters Patent are hereby corrected as shown below:

Abstract, line 16, change "in" to -- to --. Column 1, line 41, change "manufacturers" to -- manufactures --. Column 2, line 63, change "hertofore" to -- heretofore --; line 68, change "hemoglobinomenters" to -- hemoglobinometers --. Column 3, line 68, change "choride" to -- chloride --. Column 4, line 4, change "tertracetic" to -- tetracetic --; line 37, change "bu" to -- by --; line 64, change "us" to -- in use --. Column 5, line 12, change "services" to -- serves --.

Signed and Sealed this

Seventeenth Day of May 1977

[SEAL]

Attest:

RUTH C. MASON
Attesting Officer

C. MARSHALL DANN
Commissioner of Patents and Trademarks